US 11,103,829 B1

(12) United States Patent
Xue et al.

(10) Patent No.: US 11,103,829 B1
(45) Date of Patent: Aug. 31, 2021

(54) SYSTEMS AND METHODS FOR TREATING ETHYLENE OXIDE WASTE GAS

(71) Applicants: Chio Kang Medical, Inc., Palo Alto, CA (US); Qiaokang Biotech (Guangdong) Co., LTD., Guangzhou (CN)

(72) Inventors: Jianlong Xue, Guangzhou (CN); Dongxin Hou, Guangzhou (CN); Shengwei Hu, Guangzhou (CN); Yecheng He, Guangzhou (CN); Guqun Ren, Guangzhou (CN); Jiali Lin, Guangzhou (CN); Yuhua Zou, Guangzhou (CN); Qinghua Xiao, Guangzhou (CN); Lixiong Feng, Palo Alto, CA (US)

(73) Assignees: Chio Kang Medical, Inc., Palo Alto, CA (US); Qiaokang Biotech (Guangdong) Co., LTD., Guangzhou (CN)

( * ) Notice: Subject to any disclaimer, the term of this patent is extended or adjusted under 35 U.S.C. 154(b) by 0 days.

(21) Appl. No.: 17/004,903

(22) Filed: Aug. 27, 2020

Related U.S. Application Data

(63) Continuation of application No. PCT/CN2020/100144, filed on Jul. 3, 2020.

(30) Foreign Application Priority Data

Mar. 18, 2020 (CN) .......................... 202010190412.1
Mar. 18, 2020 (CN) .......................... 202020340490.0
Mar. 18, 2020 (CN) .......................... 20202034077902

(51) Int. Cl.
*A61L 2/20* (2006.01)
*A61L 2/26* (2006.01)
(Continued)

(52) U.S. Cl.
CPC .............. *B01D 53/75* (2013.01); *A61L 2/206* (2013.01); *A61L 2/26* (2013.01); *B01D 53/0446* (2013.01);
(Continued)

(58) Field of Classification Search
CPC ..... A61L 2/20; A61L 2/26; A61L 9/00; A61L 9/01; A61L 9/014; A61L 2209/00;
(Continued)

(56) References Cited

U.S. PATENT DOCUMENTS 1,954,056 A 4/1934 Miller
2,586,670 A 2/1952 Lambertsen
(Continued)

FOREIGN PATENT DOCUMENTS

CN 1223166 A 7/1999
CN 101224381 A 7/2008
(Continued)

OTHER PUBLICATIONS

International Application No. PCT/CN2020/101140 as prepared by the Chinese International Searching Authority filed Jul. 9, 2020, 59 pages.
(Continued)

*Primary Examiner* — Timothy C Vanoy
(74) *Attorney, Agent, or Firm* — Adsero IP

(57) ABSTRACT

The present disclosure discloses systems and methods for treating ethylene oxide waste gas. The system for treating ethylene oxide waste gas includes a compounding treatment assembly, an adsorption treatment assembly, and a hydration treatment assembly. The compounding treatment assembly includes a compounding tower to contain a compounding substrate, a first gas inlet, and a first gas outlet. The adsorption treatment assembly includes an adsorber to contain an adsorbent, a second gas inlet, and a second gas outlet. A first
(Continued)

connecting pipe connects the first gas outlet with the second gas inlet. The hydration treatment assembly includes a hydration tower to contain water, a third gas inlet, and a third gas outlet. A second connecting pipe connects the second gas outlet with the third gas inlet and an exhaust pipe in communication with the third gas outlet exhausts the gas from the hydration tower.

20 Claims, 9 Drawing Sheets

(51) Int. Cl.
  *B01D 53/04* (2006.01)
  *B01D 53/14* (2006.01)
  *B01D 53/18* (2006.01)
  *B01D 53/72* (2006.01)
  *B01D 53/75* (2006.01)
  *B01D 53/78* (2006.01)
  *A61L 101/44* (2006.01)

(52) U.S. Cl.
  CPC ..... *B01D 53/0454* (2013.01); *B01D 53/1412* (2013.01); *B01D 53/1437* (2013.01); *B01D 53/1487* (2013.01); *B01D 53/1493* (2013.01); *B01D 53/18* (2013.01); *B01D 53/72* (2013.01); *B01D 53/78* (2013.01); *A61L 2101/44* (2020.08); *A61L 2202/13* (2013.01); *B01D 2252/103* (2013.01); *B01D 2253/102* (2013.01); *B01D 2257/70* (2013.01); *B01D 2259/45* (2013.01)

(58) Field of Classification Search
  CPC ............. A61L 2209/10; A61L 2209/20; A61L 2209/22; A62D 3/00; A62D 3/30; A62D 3/35; A62D 3/36; A62D 2203/02; B01D 53/75; B01D 53/04; B01D 53/14; B01D 53/72; B01D 53/78; B01D 2257/702; B01D 2257/708; B01D 2257/93; B01D 2258/06; B01D 2259/4533; B01J 19/00; B01J 2219/00
  See application file for complete search history.

(56) References Cited

U.S. PATENT DOCUMENTS

| | | |
|---|---|---|
| 2,817,689 A | 12/1957 | White |
| 3,022,054 A | 2/1962 | Kotzbue |
| 3,572,397 A | 3/1971 | Hirsch et al. |
| 3,598,543 A | 8/1971 | Crosby et al. |
| 3,844,739 A | 10/1974 | Alfrey, Jr. |
| 3,961,920 A | 6/1976 | Gilbert |
| 3,997,633 A | 12/1976 | Leva et al. |
| 4,112,054 A * | 9/1978 | Feingold ............ B01D 53/72 422/34 |
| 4,119,539 A | 10/1978 | Ettel et al. |
| 4,134,425 A | 1/1979 | Gussefeld et al. |
| 4,243,636 A | 1/1981 | Shiraki et al. |
| 4,301,113 A | 11/1981 | Alguire et al. |
| 4,517,167 A | 5/1985 | Popescu et al. |
| 4,549,363 A | 10/1985 | Buonicore |
| 4,555,251 A | 11/1985 | Jonsson |
| 4,831,196 A | 5/1989 | Buonicore et al. |
| 5,084,075 A | 1/1992 | Sircar |
| 5,204,075 A | 4/1993 | Jain et al. |
| 5,270,000 A | 12/1993 | Goldner et al. |
| 5,283,035 A | 2/1994 | Karthaus et al. |
| 5,290,345 A | 3/1994 | Osendorf et al. |
| 5,511,409 A | 4/1996 | Knaebel |
| 5,522,808 A | 6/1996 | Skalla |
| 5,607,652 A | 3/1997 | Hellmuth et al. |
| 5,641,455 A | 6/1997 | Rosenlund et al. |
| 5,702,669 A | 12/1997 | Green et al. |
| 5,741,470 A * | 4/1998 | Wenzler ............. B01D 53/72 423/245.1 |
| 5,755,857 A | 5/1998 | Acharya et al. |
| 5,779,773 A | 7/1998 | Cam et al. |
| 5,964,927 A | 10/1999 | Graham et al. |
| 6,156,101 A | 12/2000 | Naheiri |
| 6,684,648 B2 | 2/2004 | Faqih |
| 6,743,402 B2 * | 6/2004 | Shimakawa ........... B01D 53/14 422/170 |
| 7,316,733 B1 | 1/2008 | Hedrick |
| 7,625,535 B2 | 12/2009 | Yamaguchi |
| 8,110,156 B2 | 2/2012 | Ricciardi et al. |
| 8,431,085 B2 | 4/2013 | Froderberg et al. |
| 9,616,143 B2 | 4/2017 | Snyder et al. |
| 10,987,443 B1 | 4/2021 | Hu et al. |
| 2002/0046569 A1 | 4/2002 | Faqih |
| 2002/0197194 A1 | 12/2002 | Machado et al. |
| 2005/0145108 A1 | 7/2005 | Rubin |
| 2006/0236860 A1 | 10/2006 | Sumida et al. |
| 2006/0249027 A1 | 11/2006 | Adolphsen et al. |
| 2007/0209383 A1 | 9/2007 | Hutton |
| 2008/0078289 A1 | 4/2008 | Sergi et al. |
| 2008/0080999 A1 | 4/2008 | Bondar |
| 2008/0289591 A1 | 11/2008 | Tessier et al. |
| 2010/0196194 A1 | 8/2010 | Voeten et al. |
| 2011/0265644 A1 | 11/2011 | Swami et al. |
| 2011/0283885 A1 | 11/2011 | Thiele |
| 2012/0031268 A1 | 2/2012 | Yaghi et al. |
| 2012/0298207 A1 | 11/2012 | Woelk et al. |
| 2014/0119989 A1 | 5/2014 | Hayashi |
| 2014/0251130 A1 | 9/2014 | Sprinkle et al. |
| 2014/0290162 A1 | 10/2014 | Tanimoto |
| 2016/0010883 A1 | 1/2016 | Jornitz et al. |
| 2017/0056813 A1 | 3/2017 | McMahon et la. |
| 2019/0076776 A1 | 3/2019 | Mahecha-Botero et al. |
| 2019/0151791 A1 | 5/2019 | Awadh et al. |
| 2019/0175971 A1 | 6/2019 | Moore et al. |
| 2020/0148655 A1 | 5/2020 | Duff et al. |

FOREIGN PATENT DOCUMENTS

| | | |
|---|---|---|
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102921570 A | 2/2013 |
| CN | 202802975 U | 3/2013 |
| CN | 202933710 U | 5/2013 |
| CN | 103394278 A | 11/2013 |
| CN | 103657383 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 204261680 U | 4/2015 |
| CN | 204447972 U | 7/2015 |
| CN | 104815535 A | 8/2015 |
| CN | 105132060 A | 12/2015 |
| CN | 105327665 A | 2/2016 |
| CN | 105664822 A | 2/2016 |
| CN | 205300112 U | 6/2016 |
| CN | 106475021 A | 3/2017 |
| CN | 106582126 A | 4/2017 |
| CN | 206535551 U | 10/2017 |
| CN | 206853397 U | 1/2018 |
| CN | 107677016 A | 2/2018 |
| CN | 207169397 U | 4/2018 |
| CN | 207187463 U | 4/2018 |
| CN | 207745676 U | 8/2018 |
| CN | 207913454 U | 9/2018 |
| CN | 108607511 A | 10/2018 |

(56) References Cited

FOREIGN PATENT DOCUMENTS

| | | |
|---|---|---|
| CN | 208218734 U | 12/2018 |
| CN | 109382064 A | 2/2019 |
| CN | 208448985 U | 2/2019 |
| CN | 208893903 U | 5/2019 |
| CN | 110145747 A | 8/2019 |
| CN | 110302634 A | 10/2019 |
| CN | 110404485 A | 11/2019 |
| CN | 209662917 U | 11/2019 |
| CN | 110833754 A | 2/2020 |
| CN | 210021633 U | 2/2020 |
| CN | 210088451 U | 2/2020 |
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| WO | WO2011002277 A1 | 1/2011 |
| WO | WO2019236249 A1 | 12/2019 |

OTHER PUBLICATIONS

U.S. Appl. No. 17/012,857, TrackOne Bypass CON Application, filed Sep. 4, 2020, 148 pages.
International Application No. PCT/CN2020/100143 as prepared by the Chinese International Searching Authority filed Jul. 3, 2020, 25 pages.
U.S. Appl. No. 17/002,500, TrackOne Bypass CON Application, filed Aug. 25, 2020, 61 pages.
International Application No. PCT/CN2020/100125 as prepared by the Chinese International Searching Authority filed Jul. 3, 2020, 27 pages.
U.S. Appl. No. 17/002,523, TrackOne Bypass CON Application, filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed Jul. 3, 2020, 22 pages.
U.S. Appl. No. 17/002,529, TrackOne Bypass CON Application, filed Aug. 25, 2020, 64 pages.
International Application No. PCT/CN2020/100119 as prepared by the Chinese International Searching Authority filed Jul. 3, 2020, 29 pages.
U.S. Appl. No. 17/002,540, TrackOne Bypass CON Application, filed Aug. 25, 2020, 89 pages.
International Application No. PCT/CN2020/100120 as prepared by the Chinese International Searching Authority filed Jul. 3, 2020, 28 pages.
U.S. Appl. No. 17/004,730, TrackOne Bypass CON Application, filed Aug. 27, 2020, 77 pages.
International Application No. PCT/CN2020/101142 as prepared by the Chinese International Searching Authority filed Jul. 9, 2020, 29 pages.
U.S. Appl. No. 17/012,864, TrackOne Bypass CON Application, filed Sep. 4, 2020, 78 pages.
International Application No. PCT/CN2020/100144 as prepared by the Chinese International Searching Authority filed Jul. 3, 2020, 24 pages.
International Application No. PCT/CN2020/100122 as prepared by the Chinese International Searching Authority filed Jul. 3, 2020, 34 pages.
U.S. Appl. No. 17/004,930, TrackOne Bypass CON Application, filed Aug. 27, 2020, 80 pages.
U.S. Appl. No. 17/004,930 Office Action-Restriction Requirement, dated Nov. 4, 2020, 6 pages.
International Application No. PCT/CN2020/100113 as prepared by the Chinese International Searching Authority filed Jul. 3, 2020, 35 pages.
U.S. Appl. No. 17/004,971, TrackOne Bypass CON Application, filed Aug. 27, 2020, 75 pages.
U.S. Appl. No. 17/012,857, Non-Final Office Action, dated Nov. 24, 2020, 13 pages.
U.S. Appl. No. 17/002,500, Non-Final Office Action dated Dec. 8, 2020, 109 pages.
Kahm et al., 2018, "Lyapunov exponents with Model Predictive Control for exothermic batch reactors" IFAC-Papers Online, 51, 417-422.
U.S. Appl. No. 17/002,523 Notice of Allowance, dated Dec. 17, 2020, 35 pages.
U.S. Appl. No. 17/002,540, Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion International Application No. PCT/CN2020,100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500, Final Office Action dated Feb. 8, 2021, 57 pages.
U.S. Appl. No. 17/004,971, Notice of Allowance, dated Feb. 8, 2021, 30 pages.
U.S. Appl. No. 17/012,857, Notice of Allowance, dated Mar. 1, 2021, 26 pages.
U.S. Appl. No. 17/002,540, Final Office Action, dated Mar. 26, 2021, 36 pages.
U.S. Appl. No. 17/004,730, Non-Final Office Action, dated Apr. 1, 2021, 30 pages.
U.S. Appl. No. 17/002,500, Non-Final Office Action dated Apr. 15, 2021, 89 pages.
U.S. Appl. No. 17/002,540, Notice of Allowance, dated Apr. 26, 2021, 21 pages.
U.S. Appl. No. 17/004,930 Notice of Allowance, dated Apr. 28, 2021, 35 pages.
U.S. Appl. No. 17/002,529 Notice of Allowance, dated May 3, 2021, 30 pages.
U.S. Appl. No. 17/002,523 Notice of Allowance, dated May 27, 2021, 26 pages.
U.S. Appl. No. 17/012,864, Notice of Allowance, dated Jun. 15, 2021, 56 pages.
U.S. Appl. No. 17/004,730, Notice of Allowance, dated Jun. 24, 2021, 30 pages.
U.S. Appl. No. 17/012,857, Notice of Allowance, dated Jun. 28, 2021, 21 pages.
U.S. Appl. No. 17/002,500, Notice of Allowance dated Jul. 8, 2021, 27 pages.

* cited by examiner

US 11,103,829 B1

SYSTEMS AND METHODS FOR TREATING ETHYLENE OXIDE WASTE GAS

CROSS-REFERENCE TO RELATED APPLICATIONS

This application is a continuation of International Application No. PCT/CN2020/100144, filed on Jul. 3, 2020, which claims the benefit of Chinese Patent Application No. CN202010190412.1, filed on Mar. 18, 2020, Chinese Patent Application No. CN202020340490.0, filed on Mar. 18, 2020, and Chinese Patent Application No. CN202020340779.2, filed on Mar. 18, 2020, the entire contents of each of which are incorporated herein by reference in their entireties for all purposes.

TECHNICAL FIELD

The present disclosure relates to the technical field of waste gas treatment, and more particularly to systems and methods for treating ethylene oxide waste gas.

BACKGROUND

Currently, in the field of low-temperature sterilization, sterilization using ethylene oxide ("EO") gas is one of the main methods used to sterilize equipment. Low-temperature sterilization using ethylene oxide gas not only is effective, but it also does not damage metal equipment. After the ethylene oxide gas is used for sterilization, the harmful ethylene oxide waste gas is generally treated by a high-altitude emission method or a combustion method.

However, the high-altitude emission method causes serious pollution to the environment. The combustion method has high requirements on related equipment, it is easy to explode when careless, and there are greater hidden dangers.

Hence, there is a need for more robust and scalable solutions for implementing sterilization technologies, and, more particularly, for implementing systems, and methods for treating ethylene oxide waste gas.

SUMMARY

One or more systems and one or more methods for treating ethylene oxide waste gas are provided according to various embodiments of the present disclosure.

A system for treating ethylene oxide waste gas might include one or more of the following components: a compounding treatment assembly, an adsorption treatment assembly, and a hydration treatment assembly. The compounding treatment assembly might include a compounding tower and a gas inlet pipe. The compounding tower is configured to contain a compounding substrate and is provided with a first gas inlet and a first gas outlet. The gas inlet pipe is in communication with the first gas inlet to supply the ethylene oxide waste gas into the compounding tower. The adsorption treatment assembly comprises an adsorber and a first connecting pipe. The adsorber is configured to contain an adsorbent and is provided with a second gas inlet and a second gas outlet. The first connecting pipe connects the first gas outlet with the second gas inlet. The hydration treatment assembly comprises a hydration tower, a second connecting pipe, and an exhaust pipe. The hydration tower is configured to contain water and is provided with a third gas inlet and a third gas outlet. The second connecting pipe connects the second gas outlet with the third gas inlet. The exhaust pipe is in communication with the third gas outlet to exhaust gas from the hydration tower.

A method for treating ethylene oxide waste gas might include one or more of the following operations: filling the ethylene oxide waste gas into the compounding tower via the gas inlet pipe, and treating the ethylene oxide waste gas via the compounding substrate, such that a concentration of ethylene oxide in the ethylene oxide waste gas treated by the compounding tower is lower than a first preset concentration; conveying the ethylene oxide waste gas treated by the compounding tower to the adsorber via a first connecting pipe and adsorbing the ethylene oxide in the ethylene oxide waste gas via the adsorbent, such that a concentration of ethylene oxide in the ethylene oxide waste gas treated by the adsorber is lower than a second preset concentration; and conveying the ethylene oxide waste gas treated by the adsorber to the hydration tower via the second connecting pipe and absorbing the ethylene oxide in the ethylene oxide waste gas via water, such that a concentration of ethylene oxide in the ethylene oxide waste gas treated by the hydration tower is lower than a third preset concentration.

These and other objects, advantages, purposes, and features will become apparent upon review of the following detailed description in conjunction with the drawings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

It will be understood that an element, when being referred to as being "fixed," "coupled," or "connected" to another element, may be directly fixed, coupled or connected to the other element or fixed, coupled or connected to the other element via an intermediate element. Such terms as "vertical," "horizontal," "left," "right," and the like used herein are for illustrative purposes only and should not be construed as limiting the implementation of the present disclosure.

Unless otherwise indicated, all numbers used herein to express quantities, dimensions, and so forth used should be understood as being modified in all instances by the term "about". In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
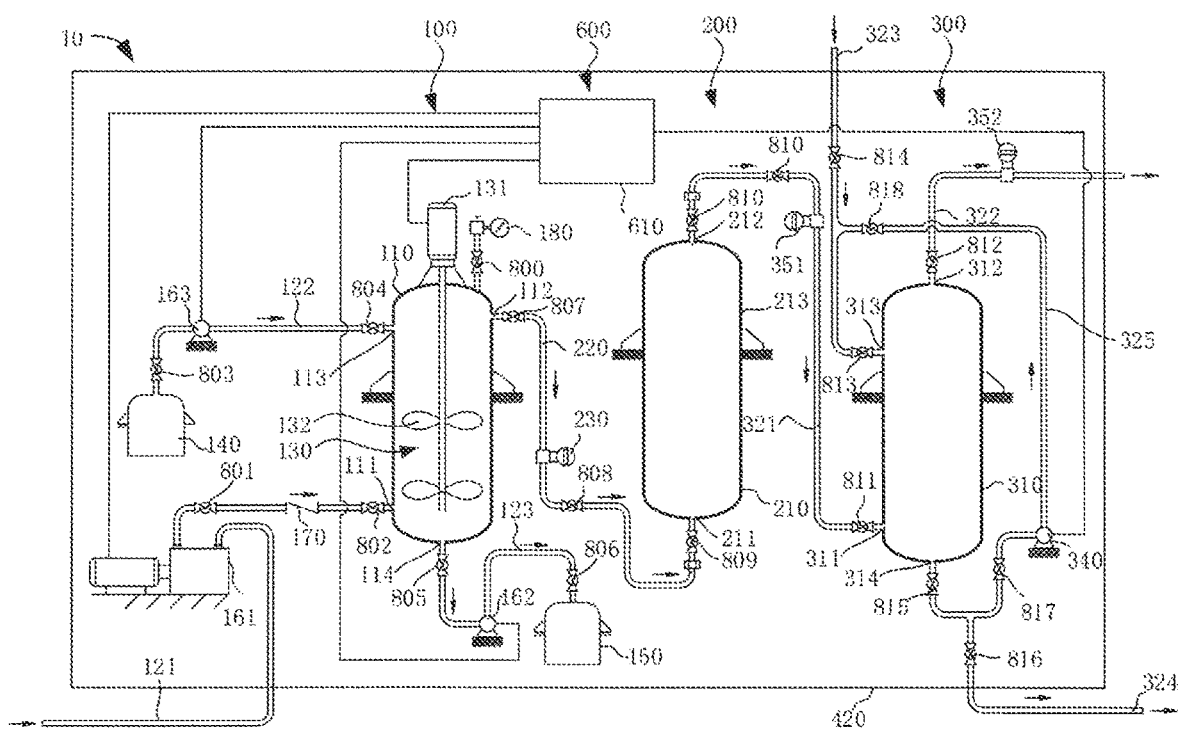
FIG. 1 is a schematic view of an ethylene oxide waste gas treatment system according to an embodiment.
Figure 2:
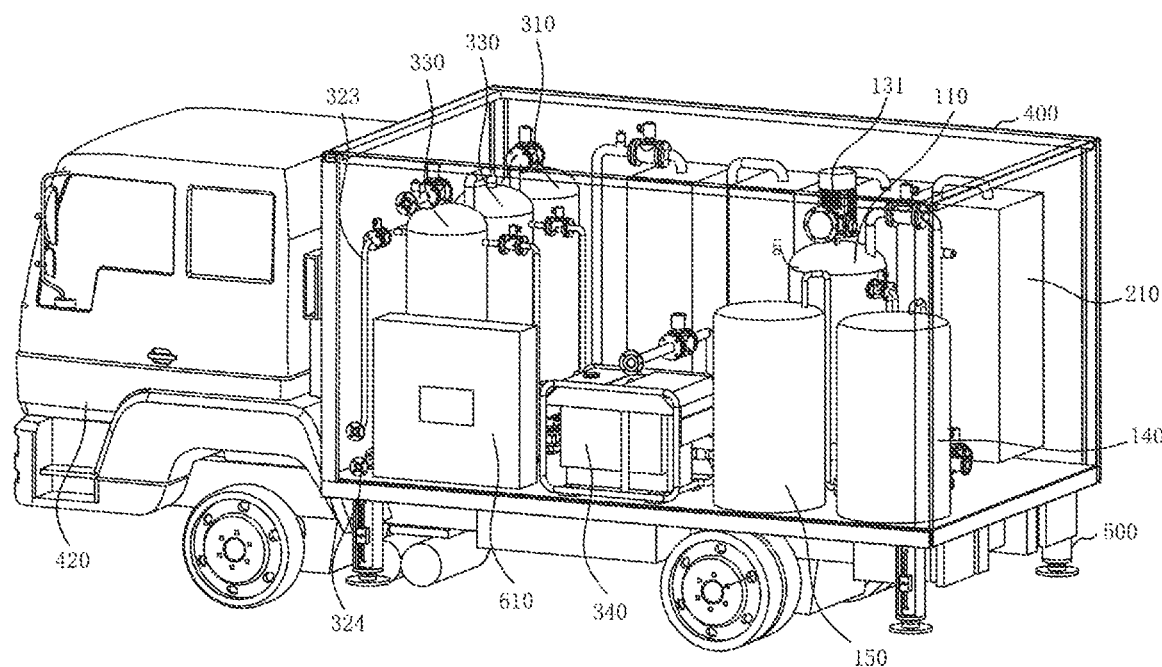
FIG. 2 is a perspective view of an ethylene oxide waste gas treatment system according to an embodiment.
Figure 3:
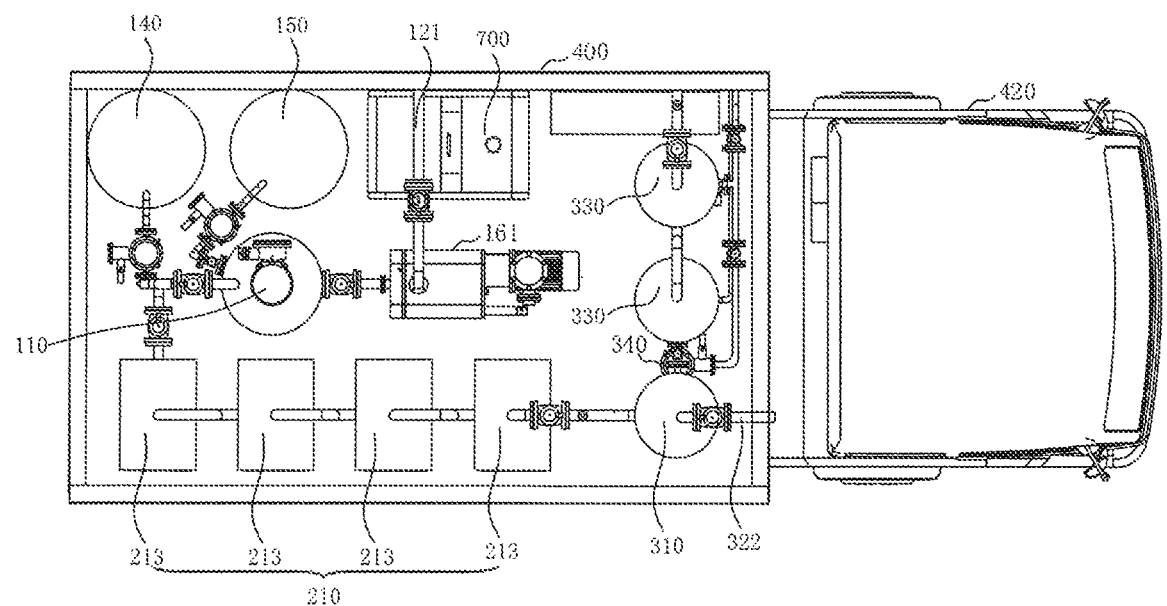
FIG. 3 is a top view of the ethylene oxide gas waste treatment system shown in FIG. 2.

As shown in FIGS. 1 to 3, an ethylene oxide waste gas treatment system 10 is provided. The ethylene oxide waste gas treatment system 10 may be a fixed system or device or an integrally movable system or device. The ethylene oxide waste gas treatment system 10 includes a compounding treatment assembly 100, an adsorption treatment assembly 200, a hydration treatment assembly 300, a moving assembly 400, a supporting assembly 500, a control assembly 600, and a power supply assembly 700. The compounding treatment assembly 100, the adsorption treatment assembly 200, the hydration treatment assembly 300, and the control assembly 600 may be mounted on the moving assembly 400. The supporting assembly 500 may be coupled to the moving assembly 400 and may be used to support the moving assembly 400. The control assembly 600 may be used to control the compounding treatment assembly 100, the adsorption treatment assembly 200, and the hydration treatment assembly 300 to perform one or more functions.

In some embodiments, the compounding treatment assembly 100 includes a compounding tower 110, an air or gas inlet pipe 121, a stirrer 130, a compounding substrate storage tank 140, a waste liquid recycle tank 150, a liquid inlet pipe 122, a liquid outlet pipe 123, a vacuum pump 161, a check valve 170, a first liquid pump 162, a second liquid pump 163, a pressure detector 180, and a plurality of valves (800-806).

The compounding tower 110 is used to contain compounding substrates. The compounding tower 110 is provided with a first air or gas inlet 111 and a first air or gas outlet 112, and the air or gas inlet pipe 121 is in communication with the first air or gas inlet 111 to supply the ethylene oxide waste gas into the compounding tower 110. In the illustrated embodiment, the first air or gas inlet 111 is located on the lower left side of the compounding tower 110, and the first air or gas outlet 112 is located on the upper right side of the compounding tower 110.

Optionally, in one embodiment, the compounding substrate contained within the compounding tower 110 may be an ethylene oxide compound complex solution, which can react with the ethylene oxide in the waste gas to remove the ethylene oxide from the waste gas. The reaction of the ethylene oxide compound complex solution with ethylene oxide is free of acid contamination and the product of the reaction is also a surfactant, which is a main component of an ionic detergent. Compared with conventional inorganic acid catalysis reactions, in the reaction of the ethylene oxide compound complex solution with ethylene oxide waste utilization is realized, resources are saved, and the reaction is green and environmentally friendly.

According to some embodiments, the ethylene oxide compound complex solution may be mainly composed of a combination of inorganic acids, sulfonic acids, and unsaturated fatty acids. In some cases, the molar ratio of inorganic acids to sulfonic acids to oleic acids may range from 1:1:1 to 1:1000:100, or the like. Alternatively, the ethylene oxide compound complex solution may include one or two of inorganic acids, sulfonic acids, or unsaturated fatty acids. In some embodiments, the inorganic acids may include, without limitation, at least one of sulfuric acid or phosphoric acid, and/or the like. According to some embodiments, the sulfonic acids may have a general formula of R—SO3H, where R is a hydrocarbyl, and may include, but are not limited to, at least one of methylsulphonic acid, ethylsulfonic acid, propylsulfonic acid, butylsulfonic acid, pentylsulfonic acid, hexylsulfonic acid, heptylsulfonic acid, octylsulfonic acid, nonylsulfonic acid, decylsulfonic acid, undecylsulfonic acid, dodecylsulfonic acid, tridecylsulfonic acid, tetradecylsulfonic acid, pentadecylsulfonic acid, hexadecylsulfonic acid, heptadecylsulfonic acid, octadecylsulfonic acid, methylsulfonic acid, ethylbenzenesulfonic acid, propylbenzenesulfonic acid, butylbenzenesulfonic acid, pentylbenzenesulfonic acid, hexylbenzenesulfonic acid, heptybenzenesulfonic acid, octylbenzenesulfonic acid, nonylbenzenesulfonic acid, decylbenzenesulfonic acid, undecylbenzenesulfonic acid, dodecylbenzenesulfonic acid, tridecylbenzenesulfonic acid, tetradecylbenzenesulfonic acid, pentadecylbenzenesulfonic acid, hexadecylbenzenesulfonic acid, heptadecylbenzenesulfonic acid, octadecylbenzenesulfonic acid, nonadecylbenzenesulfonic acid, or eicosylbenzenesulfonic acid, and/or the like Merely by way of example, in some cases, the unsaturated fatty acids might include, without limitation, at least one of oleic acid, linoleic acid, or linolenic acid, and/or the like.

The vacuum pump 161 and the check valve 170 may be provided on the gas inlet pipe 121, and the vacuum pump

161 may be located upstream of the check valve 170. The vacuum pump 161 may be used to fill the compounding tower 110 with ethylene oxide waste gas and the check valve 170 can be used to prevent the ethylene oxide waste gas from flowing backward. Thus, ensuring the safe and normal operation of the entire system 10.

The stirrer 130 includes a driving portion 131 and a stirring portion 132. The driving portion 131 may be located above the compounding tower 110, and the stirring portion 132 may be located inside the compounding tower 110. The driving portion 131 can cause the stirring portion 132 to rotate. In the illustrated embodiment, the driving portion 131 is a motor, and the stirring portion 132 includes stirring blades. The stirrer 130 can promote the mixing of the ethylene oxide waste gas with the compounding substrate and enhance the effect of the compound reaction such that most of the ethylene oxide in the waste gas is treated and removed from the ethylene oxide waste gas.

The compounding tower 110 is also provided with a liquid inlet 113 and a liquid outlet 114. The liquid inlet 113 is in communication with the liquid inlet pipe 122 and the liquid outlet 114 is in communication with the liquid outlet pipe 123. In the illustrated embodiment, the liquid inlet 113 is provided at an upper left side of the compounding tower 110 and the liquid outlet 114 is provided at a bottom portion of the compounding tower 110. The liquid inlet pipe 122 communicates the compounding substrate storage tank 140 with the compounding tower 110. The liquid outlet pipe 123 communicates the compounding tower 110 with the waste liquid recycle tank 150. The first liquid pump 162 is provided on the liquid outlet pipe 123 and the second liquid pump 163 is provided on the liquid inlet pipe 122. The waste liquid generated after the reaction of the compounding substrate with the ethylene oxide in the waste gas can be pumped from the compounding tower 110 into the waste liquid recycle tank 150 by the first liquid pump 162. Then, the compounding tower 110 may be filled with a new compounding substrate stored in the compounding substrate storage tank 140 by the second liquid pump 163 to continue the treatment of the ethylene oxide waste gas. In this way, the continuous renewal of the compounding substrate in the compounding tower 110 can be ensured and the effective treatment of the ethylene oxide waste gas can be guaranteed.

The pressure detector 180 may be used to detect the pressure inside the compounding tower 110 in real time. In the illustrated embodiment, the pressure detector 180 is provided on the top of the compounding tower 110.

The gas inlet pipe 121 may be provided with a first valve 801 and a second valve 802. The first valve 801 may be located between the vacuum pump 161 and the check valve 170 and the second valve 802 may be located between the check valve 170 and the compounding tower 110. The liquid inlet pipe 122 may be provided with a third valve 803 and a fourth valve 804. The third valve 803 may be located between the compounding substrate storage tank 140 and the second liquid pump 163 and the fourth valve 804 may be located between the second liquid pump 163 and the compounding tower 110. The liquid outlet pipe 123 may be provided with a fifth valve 805 and a sixth valve 806. The fifth valve 805 may be located between the compounding tower 110 and the first liquid pump 162. The sixth valve 806 may be located between the first liquid pump 162 and the waste liquid recycle tank 150.

The adsorption treatment assembly 200 includes an adsorber 210, a first connecting pipe 220, a first ethylene oxide concentration detector 230, and a plurality of valves (807-809). The adsorber 210 includes an absorption tower, is used to contain the adsorbent, and is provided with a second air or gas inlet 211 and a second air or gas outlet 212. The first connecting pipe 220 communicates the first air or gas outlet 112 with the second air or gas inlet 211. In the illustrated embodiment, the second air or gas inlet 211 is provided at the bottom portion of the adsorber 210 and the second air or gas outlet 212 is provided at the top portion of the adsorber 210.

Figure 4:
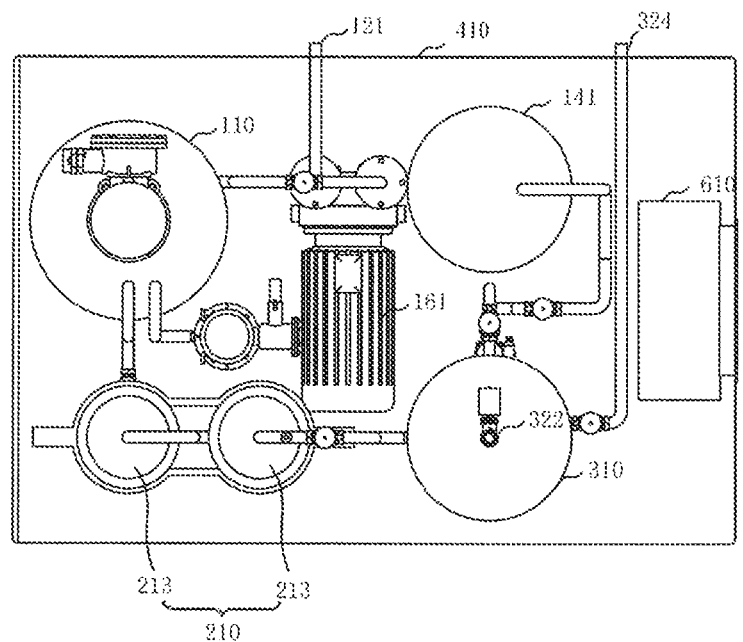
FIG. 4 is a schematic view of an ethylene oxide waste gas treatment system according to another embodiment.

Optionally, the adsorber 210 includes at least two adsorption towers 213 connected in series. In one embodiment, as shown in FIG. 3, the adsorber 210 includes four adsorption towers 213 connected in series. In another embodiment, as shown in FIG. 4, the adsorber 210 includes two adsorption towers 213 connected in series.

Optionally, the adsorbent contained within the adsorber 210 and/or adsorption tower 213 can be activated carbon. In one embodiment, the adsorbent is activated carbon. The activated carbon has the characteristics of a large specific surface area, a high strength, a uniform particle size, a developed pore structure, and a strong adsorption performance.

The first ethylene oxide concentration detector 230 may be provided on the first connecting pipe 220. The first ethylene oxide concentration detector 230 can monitor the concentration of ethylene oxide in the ethylene oxide waste gas treated by the compounding tower 110 in real time, such that, when the concentration of ethylene oxide in the treated ethylene oxide waste gas is too high, the compounding substrate can be replaced.

The first connecting pipe 220 may be provided with a seventh valve 807, an eighth valve 808, and a ninth valve 809. The seventh valve 807 may be located between the compounding tower 110 and the first ethylene oxide concentration detector 230 and the eighth valve 808 and the ninth valve 809 may be located between the first ethylene oxide concentration detector 230 and the adsorber 210.

The hydration treatment assembly 300 includes a hydration tower 310, a second connecting pipe 321, an exhaust pipe 322, a water or liquid inlet pipe 323, a water or liquid outlet pipe 324, a wastewater recycle tank 330, a water pump 340, a third connecting pipe 325, a second ethylene oxide concentration detector 351, a third ethylene oxide concentration detector 352, and a plurality of valves (810-818).

The hydration tower 310 may be used to contain water and may be provided with a third air or gas inlet 311 and a third air or gas outlet 312. The second connecting pipe 321 communicates the second air or gas outlet 212 with the third air or gas inlet 311. The exhaust pipe 322 is in communication with the third air or gas outlet 312 to exhaust the gas from the hydration tower 310. In the illustrated embodiment, the third air or gas inlet 311 is located at a lower left side of the hydration tower 310 and the third air or gas outlet 312 is located at a top portion of the hydration tower 310.

The hydration treatment assembly 300 further includes a water or liquid inlet pipe 323 and a water or liquid outlet pipe 324. The hydration tower 310 is provided with a water or liquid inlet 313 and a water or liquid outlet 314. The water or liquid inlet pipe 323 is in communication with the water or liquid inlet 313 to supply water or other liquid into the hydration tower 310 and the water or liquid outlet pipe 324 is in communication with the water or liquid outlet 314 to drain the water or other liquid from the hydration tower 310. Optionally, the end of the water or liquid inlet pipe 323 away from the water inlet 313 is in communication with an external water or liquid source (such as tap water, etc.). The water or liquid inlet pipe 323 sprays water or other liquid into the hydration tower 310 via the water or liquid inlet 313.

In the illustrated embodiment, the water or liquid inlet 313 is located at the upper left side of the hydration tower 310 and the water or liquid outlet 314 is located at the bottom portion of the hydration tower 310. Spraying water or other liquid into the hydration tower 310 via the water or liquid inlet can increase the contact area between the water or other liquid and the ethylene oxide waste gas and increase the adsorption rate of the ethylene oxide from the ethylene oxide waste gas. The wastewater that has absorbed the ethylene oxide waste gas can be drained via the water or liquid outlet pipe 324. In one embodiment, the wastewater that has absorbed the ethylene oxide waste gas may be stored in the wastewater recycle tank 330. The wastewater recycle tank 330 has a wastewater inlet and a wastewater outlet (not shown). The wastewater inlet is in communication with the water or liquid outlet 314, and the wastewater outlet is in communication with the water outlet pipe 324, such that the wastewater can be concentrated and drained.

Both ends of the third connecting pipe 325 are in communication with the water inlet pipe 323 and the water outlet pipe 324, respectively. The water pump 340 is provided on the third connecting pipe 325.

The second ethylene oxide concentration detector 351 may be provided on the second connecting pipe 321. The second ethylene oxide concentration detector 351 can monitor the concentration of ethylene oxide in the ethylene oxide waste gas treated by the adsorber 210 in real time such that, when the concentration of ethylene oxide in the treated waste gas is too high, the adsorbent can be replaced.

The third ethylene oxide concentration detector 352 may be provided on the exhaust pipe 322. The third ethylene oxide concentration detector 352 can monitor the concentration of ethylene oxide in the ethylene oxide waste gas treated by the hydration tower 310 in real time. Thus, ensuring that the ethylene oxide waste gas exhausted from the exhaust pipe 322 meets safety emission standards.

The second connecting pipe 321 may be provided with a tenth valve 810 and an eleventh valve 811. The tenth valve 810 may be located between the adsorber 210 and the second ethylene oxide concentration detector 351 and the eleventh valve 808 may be located between the second ethylene oxide concentration detector 351 and the hydration tower 310. The exhaust pipe 322 may be provided with a twelfth valve 812, located between the hydration tower 310 and the third ethylene oxide concentration detector 352. The water or liquid inlet pipe 323 may be provided with a thirteenth valve 813 and a fourteenth valve 814, which may be located on both sides of the connection point connecting the water or liquid inlet pipe 323 to the third connecting pipe 325. The water or liquid outlet pipe 324 may be provided with a fifteenth valve 815 and a sixteenth valve 816 which may be located on both sides of the connection point connecting the water or liquid outlet pipe 324 and the third connecting pipe 325. The third connecting pipe 325 may be provided with a seventeenth valve 817 and an eighteenth valve 818 which may be located on both sides of the water pump 340.

Figure 5:
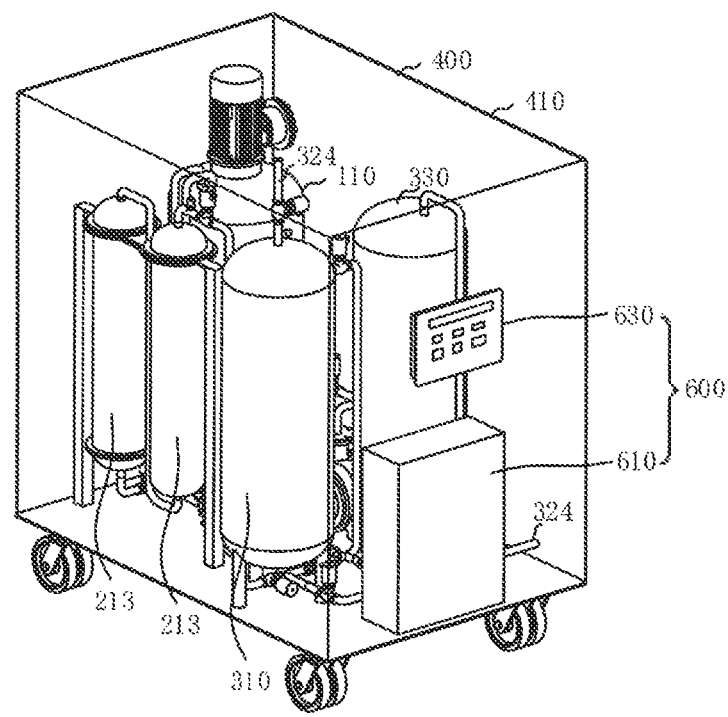
FIG. 5 is a perspective view of an ethylene oxide waste gas treatment system according to another embodiment.

The moving assembly 400 may be a moving rack 410 (shown in FIGS. 4 and 5) or a vehicle body 420 (shown in FIGS. 1-3). The entire ethylene oxide waste gas treatment system 10 can be moved quickly with the moving assembly 400, which is flexible. The ethylene oxide waste gas treatment system 10 can be moved to be connected to an ethylene oxide sterilizer to treat the ethylene oxide waste gas generated by the ethylene oxide sterilizer. At the same time, the moving assembly 400 also allows the ethylene oxide waste gas system 10 to be coupled to ethylene oxide sterilizers in the field and indoors anytime and anywhere for ethylene oxide waste gas treatment, regardless of time, place, and environment.

Optionally, the control assembly 600 includes a controller 610 and a display 630. Optionally, the controller 610 is a programmable logic controller ("PLC"). The vacuum pump 161, the first liquid pump 162, the second liquid pump 163, the water pump 340, each of the valves (e.g., valves 170 and 801-818), the driving portion 131 of the stirrer 130, the pressure detector 180, the first ethylene oxide concentration detector 230, the second ethylene oxide concentration detector 351, the third ethylene oxide concentration detector 352, and the power supply assembly 700 are electrically connected to the controller 610 (the electrical connection may be at least one of a wired electrical connection and/or a wireless communication connection). The controller 610 can control the aforementioned vacuum pump 161, first liquid pump 162, second liquid pump 163, water pump 340, driving unit 131 of the stirrer 130, and the power supply assembly 700 to perform one or more functions. The controller 610 also controls the opening and closing of each valve (e.g., valves 170 and 801-818), and the processing of data fed back by the pressure detector 180, the first ethylene oxide concentration detector 230, the second ethylene oxide concentration detector 351, and the third ethylene oxide concentration detector 352. The control of each of the components by the controller 610 realizes real-time monitoring and control of the treatment process of the ethylene oxide waste gas, the full automation saves manpower costs, and intelligent control improves the safety of ethylene oxide waste gas treatment. The display 630 is used to display the operation status and operation data of the aforementioned components.

In operation, the ethylene oxide waste gas in the aforementioned ethylene oxide waste gas treatment system 10 enters the compounding tower 110 via the gas inlet pipe 121, and the compounding substrate in the compounding tower 110 can react with the ethylene oxide in the ethylene oxide waste gas to remove most of the ethylene oxide in the ethylene oxide waste gas. The ethylene oxide waste gas treated by the compounding tower 110 then enters the adsorber 210 through the first connecting pipe 220, and the adsorbent in the adsorber 210 adsorbs most of the remaining ethylene oxide in the ethylene oxide waste gas, further reducing the concentration of ethylene oxide in the ethylene oxide waste gas. Next, the ethylene oxide waste gas treated by the adsorber 210 enters the hydration tower 310 via the second connecting pipe 321 and the water in the hydration tower 310 absorbs most of the residual ethylene oxide in the ethylene oxide waste gas. Finally, the ethylene oxide waste gas that meets the emission requirements after the three stages of treatment by the compounding tower 110, the adsorber 210, and the hydration tower 310 is exhausted from the exhaust pipe 322 of the hydration tower 310. In the ethylene oxide waste gas treatment system 10, by allowing the ethylene oxide waste gas to pass through the compounding tower 110, the adsorber 210, and the hydration tower 310 for three stages of treatment, the highly efficient treatment of the ethylene oxide waste gas at normal temperature and pressure is achieved, and the safety emission requirements is met. The ethylene oxide waste gas treatment system 10 is simple, safe, and reliable, and will not cause secondary pollution to the environment.

Figure 6:
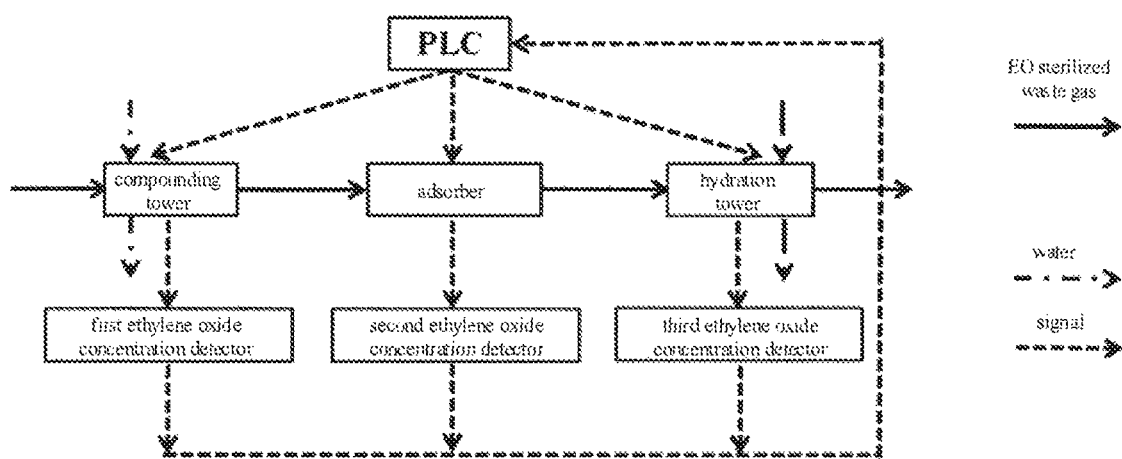
FIG. 6 is a schematic view of the control of an ethylene oxide waste gas treatment system according to yet another embodiment.

FIG. 6 is a schematic view of the control of an ethylene oxide waste gas treatment system according to yet another embodiment. There is also provided a method for treating ethylene oxide waste gas, which can be achieved by using the aforementioned ethylene oxide waste gas treatment system 10. The method includes the following steps:

Step S1: the compounding tower 110 is filled with the ethylene oxide waste gas via the gas inlet pipe 121, and the ethylene oxide in the ethylene oxide waste gas is treated via the compounding substrate in the compounding tower 110 such that a concentration of ethylene oxide in the ethylene oxide waste gas exhausted from the compounding tower 110 is lower than a first preset concentration.

The first preset concentration may range from about 3% Vol to about 5% a Vol.

Optionally, step S1 further includes the following steps:

If the concentration of ethylene oxide detected in the ethylene oxide waste gas by the first ethylene oxide concentration detector 230 is greater than the first preset concentration, the operation of the compounding tower 110 is stopped, the compounding substrate waste liquid in the compounding tower 110 is drained to the waste liquid recycle tank 150 via the liquid outlet pipe 123 and a new compounding substrate from the compounding substrate storage tank 140 is used to fill the compounding tower 110 via the liquid inlet pipe 122. Once the compounding tower 110 is filled with the new compounding substrate, then, the compounding tower 110 is restarted.

Optionally, if the concentration of ethylene oxide detected in the ethylene oxide waste gas by the first ethylene oxide concentration detector 230 is greater than the first preset concentration, the first ethylene oxide concentration detector 230 feeds back the signal to the controller 610 in real time. The controller 610 controls the compounding tower 110 to stop operating according to the received signal, the compounding substrate waste liquid in the compounding tower 110 is drained to the waste liquid recycle tank 150 via the liquid outlet pipe 123 and the new compounding substrate in the compounding substrate storage tank 140 is added to the compounding tower 110 via the liquid inlet pipe 122. Then, the compounding tower 110 is restarted by the controller 610.

The aforementioned steps can ensure that the compounding substrate in the compounding tower 110 is renewed to maintain the compounding treatment capacity of the compounding tower 110, and to ensure that the concentration of ethylene oxide in the waste gas treated by the compounding tower 110 is lower than the first preset concentration.

Step S2: the ethylene oxide waste gas treated by the compounding tower 110 is conveyed to the adsorber 210 via a first connecting pipe 220, and the ethylene oxide in the ethylene oxide waste gas is adsorbed via the adsorbent in the adsorber 210 such that a concentration of ethylene oxide in the ethylene oxide waste gas exhausted from the adsorber 210 is lower than a second preset concentration.

The second preset concentration may range from about 1900 ppm to about 2100 ppm.

Optionally, step S2 further includes the following steps:

If the concentration ethylene oxide detected in the ethylene oxide waste gas by the second ethylene oxide concentration detector 351 is greater than the second preset concentration, the operation of the adsorber 210 is stopped, the adsorbent in the adsorber 210 is replaced, and the adsorber 210 is restarted.

Optionally, if the concentration of ethylene oxide detected in the ethylene oxide waste gas by the second ethylene oxide concentration detector 351 is greater than the second preset concentration, the second ethylene oxide concentration detector 351 feeds back the signal to the controller 610 in real time. The controller 610 controls the adsorber 210 to stop operating according to the received signal, and controls the adsorber 210 to replace the adsorbent in the adsorber 210, and then controls the adsorber 210 to restart.

The aforementioned steps can ensure that the adsorbent in the adsorber 210 is renewed to maintain the adsorption treatment capacity of the adsorber 210 and to ensure that the concentration of ethylene oxide in the ethylene oxide waste gas treated by the adsorber 210 is lower than the second preset concentration.

Step S3: the ethylene oxide waste gas treated by the adsorber 210 is conveyed to the hydration tower 310 via a second connecting pipe 321, and the ethylene oxide in the ethylene oxide waste gas is absorbed via water in the hydration tower, such that a concentration of ethylene oxide in the ethylene oxide waste gas exhausted from the hydration tower 310 is lower than a third preset concentration.

The third preset concentration may range from about 90 ppm to about 110 ppm.

The aforementioned ethylene oxide waste gas treatment method has at least the following technical effects:

In the aforementioned method for treating ethylene oxide waste gas, by allowing the ethylene oxide waste gas to pass through the compounding tower 110, the adsorber 210, and the hydration tower 310 for three stages of treatment, highly efficient treatment of the ethylene oxide waste gas at normal temperature and pressure is achieved and the safety emission requirements are met. This method has low requirements on related devices and the devices are simple. The method is safe and reliable and will not cause secondary pollution to the environment.

The method disclosed herein is better than the conventional single acid catalytic treatment. The conventional single acid catalytic treatment cannot completely treat the high-concentration (40% to 60%) ethylene oxide waste gas immediately after sterilization under normal temperature and pressure. Similarly, the adsorption of a single activated carbon cannot complete the absorption of ethylene oxide with higher concentrations. In the system and method for treating ethylene oxide waste gas provided in the aforementioned embodiments, more than 99.99% of ethylene oxide in the sterilized ethylene oxide waste gas can be treated and removed after three stages of treatment in the compounding tower 110, the adsorber 210, and the hydration tower 310. The concentration of ethylene oxide in the exhaust gas emitted from the hydration tower 310 is below 100 ppm, which is suitable for the harmless treatment of ethylene oxide waste gas in the ethylene oxide sterilization and distribution center, achieving zero emission of ethylene oxide and the pursuit of environmental and ecological friendliness.

The following describes the system and method for treating ethylene oxide waste gas of the present disclosure in detail with reference to specific embodiments.

Example 1

A method for treating ethylene oxide waste gas included the following steps:

(1) The controller 610 controlled the vacuum pump 161 to start and fill the ethylene oxide waste gas with a volume concentration of 44% into the compounding tower 110 via the gas inlet pipe 121. The ethylene oxide in the ethylene oxide waste gas was treated by the ethylene oxide compound complex solution in the compounding tower 110. The first ethylene oxide concentration detector 230 monitored the concentration of ethylene oxide in the ethylene oxide waste gas treated by the compounding tower 110 online in real time.

(2) The remaining ethylene oxide waste gas treated by the compounding tower 110 entered the adsorber 210 via the first connecting pipe 220, and the ethylene oxide in the ethylene oxide waste gas was adsorbed by the activated carbon in the adsorber 210. The second ethylene oxide concentration detector 351 monitored the concentration of ethylene oxide in the ethylene oxide waste gas after adsorbing online in real time.

(3) The residual ethylene oxide waste gas from the adsorber 210 entered the hydration tower 310 via the second connecting pipe 321, the ethylene oxide in the ethylene oxide waste gas was absorbed and treated via water. The wastewater containing ethylene oxide was drained from the water outlet pipe 324 of the hydration tower 310, the remaining ethylene oxide waste gas was exhausted from the exhaust pipe 322. The third ethylene oxide concentration detector 352 monitored the concentration of ethylene oxide in the ethylene oxide waste gas after absorption online in real time.

After the ethylene oxide waste gas was treated by and extracted from the compounding tower 110, the ethylene oxide waste gas entered the adsorber 210. When the concentration of ethylene oxide in the ethylene oxide waste gas detected by the first ethylene oxide concentration detector 230 reached 2000 ppm, the concentrations of ethylene oxide treated by the adsorber 210 and the hydration tower 310 were recorded respectively. These concentrations were monitored and detected by the second ethylene oxide concentration detector 351 and the third ethylene oxide concentration detector 352, and the results are shown in FIGS. 7, 8, and 9.

Figure 7:
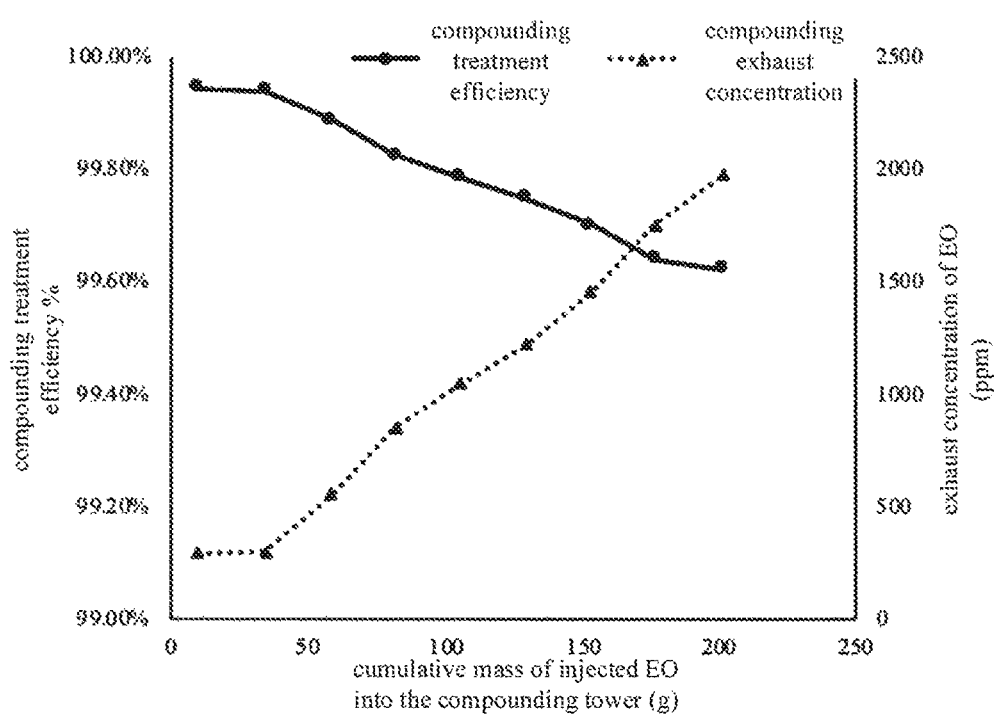
FIG. 7 is a graph showing the effect of the compounding treatment of an ethylene oxide waste gas treatment system.
Figure 8:
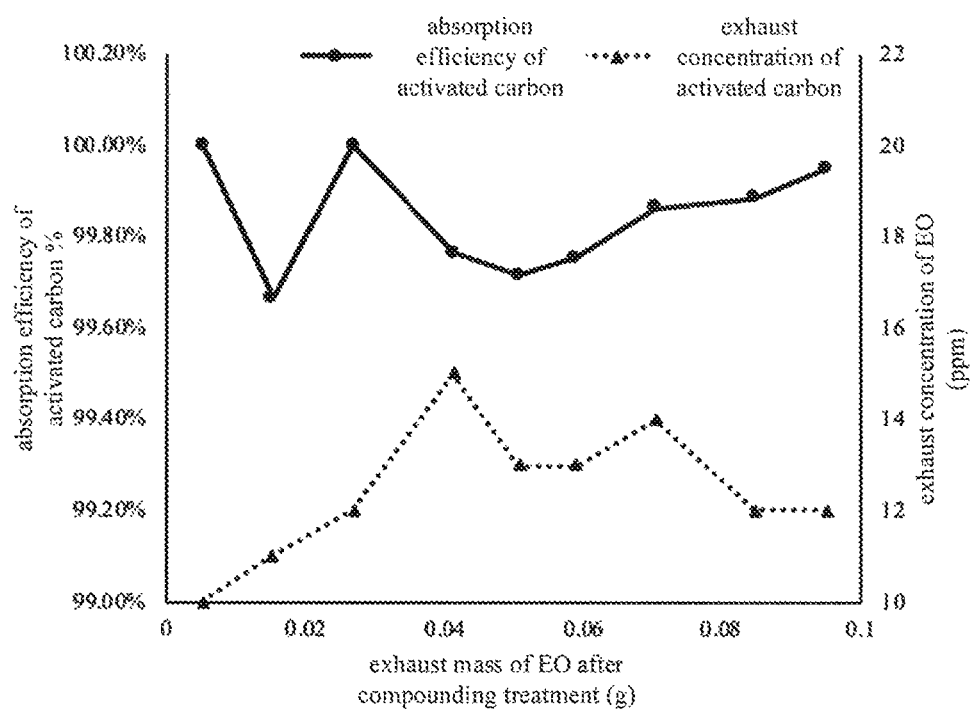
FIG. 8 is a graph showing the effect of the adsorption treatment of an ethylene oxide waste gas treatment system.
Figure 9:
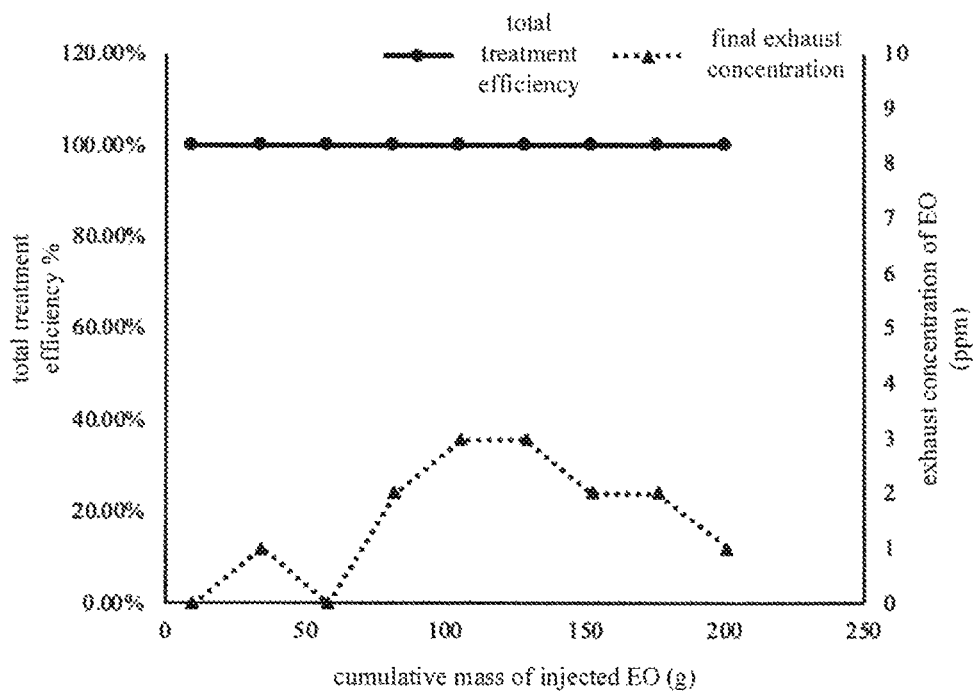
FIG. 9 is a graph showing the effect of the overall treatment of an ethylene oxide waste gas treatment system.

It can be seen from the treatment effects in FIGS. 7, 8, and 9 that, when the exhaust concentration of 44% ethylene oxide waste gas treated by the compounding tower 110 reached 2000 ppm, the concentration of ethylene oxide in the exhaust gas increased with the increase of the mass of ethylene oxide. The exhaust gas after the compounding treatment entered the adsorber 210 and the concentration of ethylene oxide in the exhaust gas after the adsorption treatment was less than 20 ppm. After the hydration treatment, the concentration of ethylene oxide in the exhaust gas was below 5 ppm.

The treatment efficiency of the ethylene oxide by the compounding tower 110 and the adsorber 210 (i.e., the percentage of mass of ethylene oxide treated in real time accounted for the mass of the filled ethylene oxide) was above 99%. The treatment efficiency of the compounding tower 110 (i.e., the percentage of cumulative treatment mass of ethylene oxide accounted for the mass of ethylene oxide compound complex) is 4%.

More than 99.999% of ethylene oxide in the sterilized waste gas could be treated and removed after three stages of treatment in the compounding tower 110, the adsorber 210, and the hydration tower 310. The concentration of ethylene oxide in the exhaust gas was below 5 ppm.

Example 2

A method for treating ethylene oxide waste gas included the following steps:

(1) The controller 610 controlled the vacuum pump 161 to start and fill the ethylene oxide waste gas with a volume concentration of 44% into the compounding tower 110 via the gas inlet pipe 121. The ethylene oxide in the ethylene oxide waste gas was treated by the ethylene oxide compound complex solution in the compounding tower 110. The first ethylene oxide concentration detector 230 monitored the concentration of ethylene oxide in the ethylene oxide waste gas treated by the compounding tower 110 in real time.

(2) The remaining ethylene oxide waste gas treated by the compounding tower 110 entered the adsorber 210 via the first connecting pipe 220, and the ethylene oxide in the ethylene oxide waste gas was adsorbed by the activated carbon in the adsorber 210. The second ethylene oxide concentration detector 351 monitored the concentration of ethylene oxide in the ethylene oxide waste gas after adsorbing in real time.

(3) The residual ethylene oxide waste gas from the adsorber 210 entered the hydration tower 310 via the second connecting pipe 321 and the ethylene oxide in the ethylene oxide waste gas was absorbed and treated via water. The wastewater containing ethylene oxide was drained from the water outlet pipe 324, the remaining ethylene oxide waste gas was exhausted from the exhaust pipe 322. The third ethylene oxide concentration detector 352 monitored the concentration of ethylene oxide in the ethylene oxide waste gas after absorption in real time.

After the ethylene oxide waste gas was treated by and extracted from the compounding tower 110, the ethylene oxide waste gas entered the adsorber 210. When the concentration of ethylene oxide in the ethylene oxide waste gas detected by the first ethylene oxide concentration detector 230 reached 4%, the concentrations of ethylene oxide in the waste gas treated by the adsorber 210 and the hydration tower 310 were recorded respectively. These concentrations were monitored by the first ethylene oxide concentration detector 230 and the second ethylene oxide concentration detector 351.

When the volume concentration of ethylene oxide detected in the ethylene oxide waste gas by the first ethylene oxide concentration detector 230 reached 4%, the controller 610 turned off the vacuum pump 161 and the stirrer 130, the first liquid pump 162 was turned on, and the ethylene oxide compound complex waste liquid in the compounding tower 110 was pumped into the waste liquid recycle tank 150 via the first connecting pipe 220. After the ethylene oxide compound complex waste liquid in the compounding tower 110 was emptied, the controller 610 controlled the second liquid pump 163 to be turned on, and the ethylene oxide compound complex solution in the compounding substrate storage tank 140 was pumped into the compounding tower 110, when the liquid level reached the lower edge of the liquid inlet, the pumping was stopped, and the system worked again.

Figure 10:
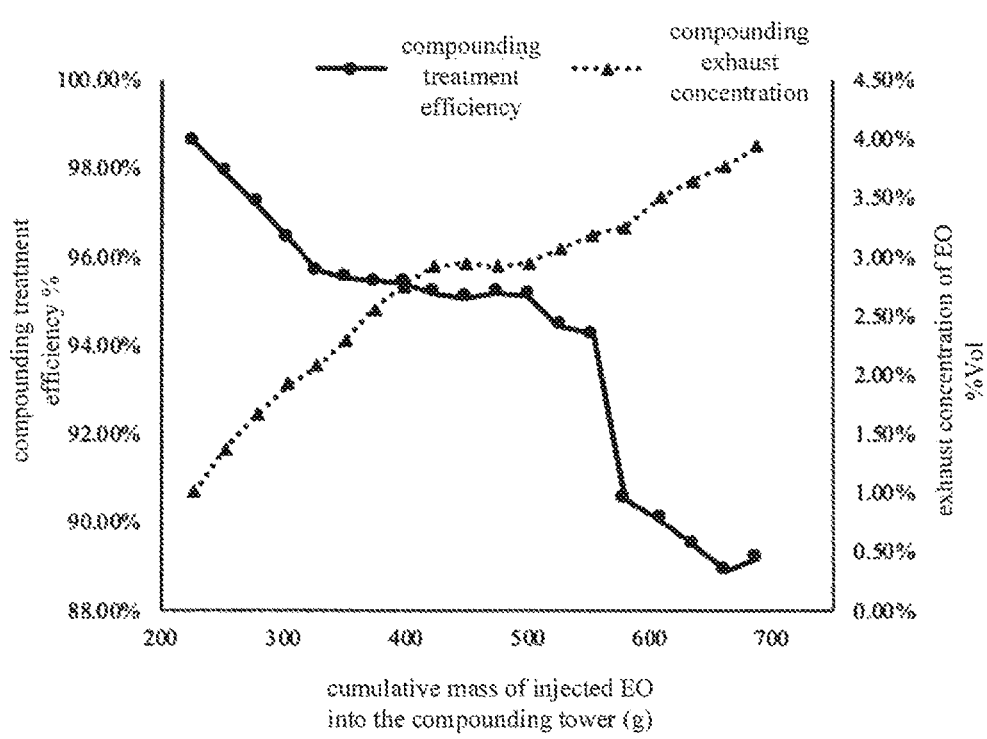
FIG. 10 is a graph showing the effect of the compounding treatment of an ethylene oxide waste gas treatment system.
Figure 11:
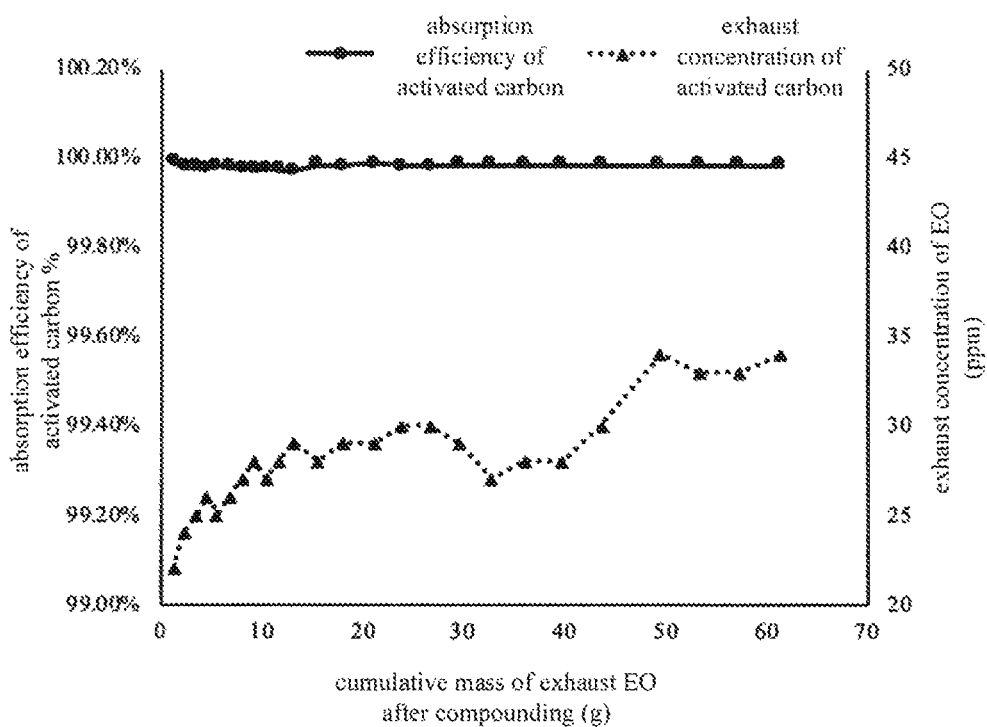
FIG. 11 is a graph showing the effect of the adsorption of an ethylene oxide waste gas treatment system.
Figure 12:
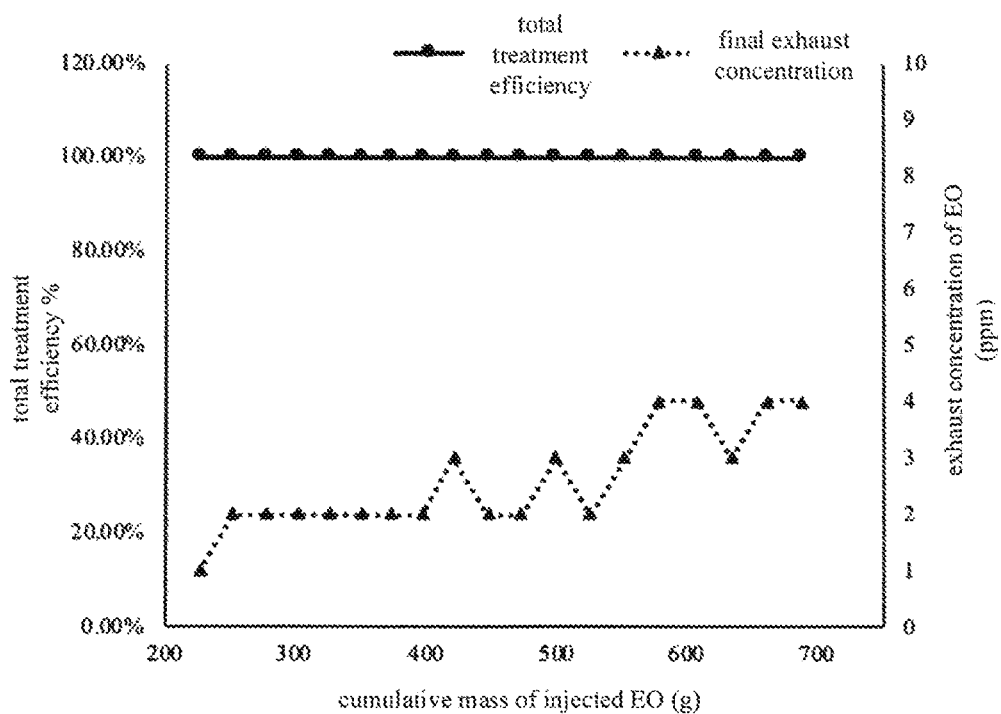
FIG. 12 is a graph showing the effect of the overall treatment of an ethylene oxide waste gas treatment system.

It can be seen from the results in FIGS. 10, 11, and 12 that, when the exhaust concentration of ethylene oxide with a volume concentration of 44% treated by the compounding tower 110 reached 4%, the concentration of ethylene oxide in the exhaust gas increased with the increase of the mass of ethylene oxide. The exhaust gas after the compounding treatment entered the adsorber 210 and the concentration of ethylene oxide in the exhaust gas after the adsorption treatment was less than 40 ppm. After the hydration treatment, the concentration of ethylene oxide in the exhaust gas was below 5 ppm.

The treatment efficiencies of the ethylene oxide by the compounding tower 110 and the adsorber 210 (i.e., the percentage of mass of ethylene oxide treated in real time accounted for the mass of the filled ethylene oxide) were both above 99%. The treatment efficiency of the compounding tower 110 (i.e., the percentage of cumulative treatment mass of ethylene oxide accounted for the mass of ethylene oxide compound complex) is 10%.

More than 99.999% of ethylene oxide in the sterilized waste gas could be treated and removed after three stages of treatment in the compounding tower 110, the adsorber 210, and the hydration tower 310. The concentration of ethylene oxide in the exhaust gas was below 5 ppm.

Example 3

A method for treating ethylene oxide waste gas included the following steps:

(1) The controller 610 controlled the vacuum pump 161 to start and fill the ethylene oxide waste gas with a volume concentration of 44% into the compounding tower 110 through the gas inlet pipe 121. The ethylene oxide in the ethylene oxide waste gas was treated by the ethylene oxide compound complex solution in the compounding tower 110. The first ethylene oxide concentration detector 230 monitored the concentration of ethylene oxide in the treated ethylene oxide waste gas in real time.

(2) The remaining ethylene oxide waste gas treated by the compounding tower 110 entered the adsorber 210 via the second connecting pipe 321 and the ethylene oxide in the ethylene oxide waste gas was adsorbed by the activated carbon in the adsorber 210. The second ethylene oxide concentration detector 351 monitored the concentration of ethylene oxide in the ethylene oxide waste gas after adsorbing in real time.

(3) The residual ethylene oxide waste gas after adsorbing entered the hydration tower 310 via the second connecting pipe 321 and the ethylene oxide in the ethylene oxide waste gas was absorbed and treated via water. The wastewater containing ethylene oxide was drained from the water outlet pipe 324, the remaining ethylene oxide waste gas was exhausted from the exhaust pipe 322. The third ethylene oxide concentration detector 352 monitored the concentration of ethylene oxide in the ethylene oxide waste gas after absorption in real time.

When the ethylene oxide waste gas was treated by and exhausted from the adsorber 210 and when the concentration of ethylene oxide in the extract gas detected by the second ethylene oxide concentration detector 351 reached 2000 ppm, the concentrations of ethylene oxide treated by the hydration tower 210 were recorded. These concentrations were detected by the third ethylene oxide concentration detector 352.

When the second ethylene oxide concentration detector 351 detected that the concentration of ethylene oxide reached 2000 ppm, the controller 610 controlled the vacuum pump 161 and the stirrer 130 to be turned off, the activated carbon in the adsorber 210 was replaced, the controller 610 controlled the vacuum pump 161 and the stirrer 130 to turn back on, and the system was restarted.

It can be seen from the results in FIGS. 11 and 12 that, when the ethylene oxide sterilized waste gas with a volume concentration of 44% was treated in three stages by the compounding tower 110, the adsorber 210 and the hydration tower 310, the concentration of ethylene oxide in the exhaust gas increased with the increase of the mass of the filled ethylene oxide. When the concentration of ethylene oxide in the exhaust gas treated by the adsorber 210 was less than 2000 ppm, the concentration of ethylene oxide in the exhaust gas after the hydration treatment was below 100 ppm. The treatment efficiencies of the ethylene oxide by the compounding tower 110 and the adsorber 210 (i.e., the percentage of mass of ethylene oxide treated in real time accounted for the mass of the filled ethylene oxide) were both above 99%. The treatment efficiency of the adsorber 210 (i.e., the percentage of cumulative treatment mass of ethylene oxide accounted for the mass of ethylene oxide compound complex) was 10%.

Figure 13:
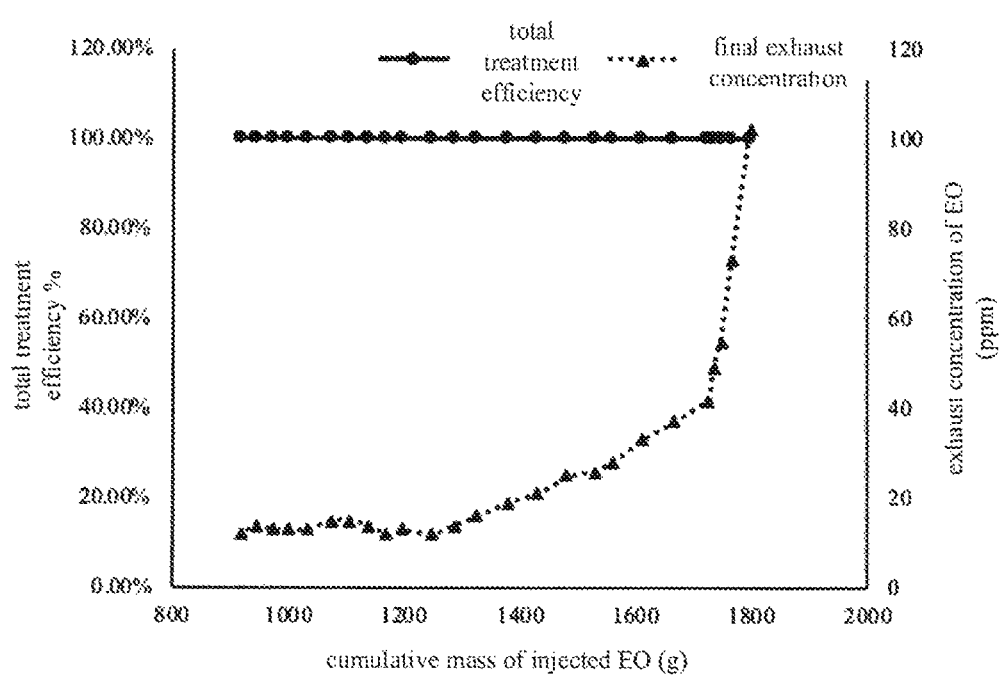
FIG. 13 is a graph showing the effect of the overall treatment of an ethylene oxide waste gas treatment system.

As shown in FIG. 13, more than 99.99% of ethylene oxide in the sterilized ethylene oxide waste gas could be treated and removed after three stages of treatment in the compounding tower 110, the adsorber 210, and the hydration tower 310. The concentration of ethylene oxide in the exhaust gas was below 100 ppm.

In summary, the systems, and methods for treating ethylene oxide waste gas provided by the present disclosure realize the real-time monitoring and control of the treatment process of ethylene oxide waste gas through the control of the controller 610. This full automation saves the labor cost and the intelligent control system improves the safety of ethylene oxide waste gas treatment.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system for treating ethylene oxide waste gas, comprising:
   a compounding treatment assembly comprising:
      a compounding tower configured to contain a compounding substrate and comprising a first gas inlet and a first gas outlet; and
      a gas inlet pipe in communication with the first gas inlet to supply the ethylene oxide waste gas into the compounding tower;
   an adsorption treatment assembly comprising:

an adsorber configured to contain an adsorbent and comprising a second gas inlet and a second gas outlet; and
a first connecting pipe connecting the first gas outlet with the second gas inlet; and
a hydration treatment assembly comprising:
a hydration tower configured to contain water and comprising a third gas inlet and a third gas outlet;
a second connecting pipe connecting the second gas outlet with the third gas inlet; and
an exhaust pipe in communication with the third gas outlet to exhaust gas from the hydration tower.

2. The ethylene oxide waste gas treatment system according to claim 1, wherein the compounding treatment assembly further comprises:
a stirrer comprising a stirring portion located inside the compounding tower and a driving portion that causes the stirring portion to rotate.

3. The ethylene oxide waste gas treatment system according to claim 1, wherein the compounding treatment assembly further comprises:
a compounding substrate storage tank;
a waste liquid recycle tank;
a liquid inlet pipe connecting the compounding substrate storage tank with the compounding tower; and
a liquid outlet pipe connecting the compounding tower with the waste liquid recycle tank.

4. The ethylene oxide waste gas treatment system according to claim 1, wherein the compounding treatment assembly further comprises:
a vacuum pump and a check valve that are provided on the gas inlet pipe, wherein the vacuum pump is located upstream of the check valve.

5. The ethylene oxide waste gas treatment system according to claim 3, wherein the compounding assembly further comprises:
a first liquid pump provided on the liquid outlet pipe; and
a second liquid pump provided on the liquid inlet pipe.

6. The ethylene oxide waste gas treatment system according to claim 1, wherein the compounding assembly further comprises:
a pressure detector provided on the compounding tower and configured to detect a pressure inside the compounding tower.

7. The ethylene oxide waste gas treatment system according to claim 1, wherein the hydration treatment assembly further comprises:
a water inlet pipe and a water outlet pipe, wherein the hydration tower comprises a water inlet and a water outlet, wherein the water inlet pipe is in communication with the water inlet to supply water into the hydration tower, and wherein the water outlet pipe is in communication with the water outlet to drain the water from the hydration tower.

8. The ethylene oxide waste gas treatment system according to claim 7, wherein the water inlet is located above the water outlet, and wherein the water inlet pipe sprays water into the hydration tower via the water inlet.

9. The ethylene oxide waste gas treatment system according to claim 7, wherein the hydration treatment assembly further comprises:
a wastewater recycle tank comprising a wastewater inlet and a wastewater outlet, wherein the wastewater inlet is in communication with the water outlet, and wherein the wastewater outlet is in communication with the water outlet pipe.

10. The ethylene oxide waste gas treatment system according to claim 7, further comprising:
a third connecting pipe in communication with the water inlet pipe and the water outlet pipe; and
a water pump provided on the third connecting pipe.

11. The ethylene oxide waste gas treatment system according to claim 1, further comprising:
a first ethylene oxide concentration detector provided on the first connecting pipe;
a second ethylene oxide concentration detector provided on the second connecting pipe; and
a third ethylene oxide concentration detector provided on the exhaust pipe.

12. The ethylene oxide waste gas treatment system according to claim 1, wherein the compounding substrate is an ethylene oxide compound complex and the adsorbent is activated carbon, wherein the ethylene oxide compound complex comprises at least one of inorganic acids, sulfonic acids, or unsaturated fatty acids.

13. The ethylene oxide waste gas treatment system according to claim 1, further comprising:
a moving assembly, wherein the compounding treatment assembly, the adsorption treatment assembly, and the hydration treatment assembly are mounted on the moving assembly.

14. The ethylene oxide waste gas treatment system according to claim 13, wherein the moving assembly is a vehicle body.

15. The ethylene oxide waste gas treatment system according to claim 13, further comprising:
a supporting assembly provided below the moving assembly.

16. The ethylene oxide waste gas treatment system according to claim 1, further comprising:
a controller, wherein the compounding tower, the adsorber, and the hydration tower are electrically coupled with the controller, and wherein the controller is configured to control the compounding tower, the adsorber, and the hydration tower to perform one or more functions.

17. A method for treating ethylene oxide waste gas, comprising:
filling a compounding tower with the ethylene oxide waste gas via a gas inlet pipe and treating ethylene oxide in the ethylene oxide waste gas via a compounding substrate contained within the compounding tower to cause a concentration of the ethylene oxide in the ethylene oxide waste gas treated by the compounding tower to be lower than a first preset concentration;
conveying the ethylene oxide waste gas treated by the compounding tower to an adsorber via a first connecting pipe and adsorbing the ethylene oxide in the ethylene oxide waste gas via an adsorbent contained within the adsorber to cause a concentration of the ethylene oxide in the ethylene oxide waste gas treated by the adsorber to be lower than a second preset concentration; and
conveying the ethylene oxide waste gas treated by the adsorber to a hydration tower via a second connecting pipe and absorbing the ethylene oxide in the ethylene oxide waste gas via water contained within the hydration tower to cause a concentration of the ethylene oxide in the ethylene oxide waste gas treated by the hydration tower to be lower than a third preset concentration.

18. The method according to claim 17, wherein the first preset concentration ranges from about 3% Vol to about 5%

Vol, the second preset concentration ranges from about 1900 ppm to about 2100 ppm, and the third preset concentration ranges from about 90 ppm to about 110 ppm.

19. The method according to claim 17, further comprising:
when the concentration of the ethylene oxide in the ethylene oxide waste gas treated by the compounding tower is higher than the first preset concentration, stopping an operation of the compounding tower, discharging the compounding substrate in the compounding tower into a waste liquid recycle tank via a liquid outlet pipe, filling the compounding tower with a new compounding substrate via a liquid inlet pipe, and restarting the operation of the compounding tower.

20. The method according to claim 17, further comprising:
when the concentration of the ethylene oxide in the ethylene oxide waste gas treated by the adsorber is higher than the second preset concentration, stopping an operation of the adsorber, replacing the adsorbent in the adsorber, and restarting the operation of the adsorber.

* * * * *